US009999451B2

(12) United States Patent
Biedermann et al.

(10) Patent No.: US 9,999,451 B2
(45) Date of Patent: Jun. 19, 2018

(54) EXTENSION DEVICE FOR A BONE ANCHOR

(71) Applicant: Biedermann Technologies GmbH & Co. KG, Donaueschingen (DE)

(72) Inventors: Timo Biedermann, Trossingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days. days.

(21) Appl. No.: 15/183,641

(22) Filed: Jun. 15, 2016

(65) Prior Publication Data

US 2016/0367295 A1  Dec. 22, 2016

Related U.S. Application Data

(60) Provisional application No. 62/180,482, filed on Jun. 16, 2015.

(30) Foreign Application Priority Data

Jun. 16, 2015  (EP) ..................................... 15172334

(51) Int. Cl.
*A61B 17/70* (2006.01)
(52) U.S. Cl.
CPC ...... *A61B 17/7085* (2013.01); *A61B 17/7032* (2013.01); *A61B 17/7076* (2013.01); *A61B 17/708* (2013.01); *A61B 17/7091* (2013.01)
(58) Field of Classification Search
CPC ................................... A61B 17/7083–17/7088
See application file for complete search history.

(56) References Cited

U.S. PATENT DOCUMENTS

| 8,439,924 B1 * | 5/2013 | McBride | A61B 17/708 606/104 |
| RE45,338 E * | 1/2015 | Chin | A61B 17/7032 606/246 |

(Continued)

FOREIGN PATENT DOCUMENTS

| EP | 2 022 423 A1 | 2/2009 |
| EP | 2 191 780 A1 | 6/2010 |

(Continued)

OTHER PUBLICATIONS

European Search Report dated Dec. 1, 2015 for Application No. 15172334.3; (7 Pages).

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

An extension device for a bone anchor includes at least one tab, which includes an elongate shaft portion that forms part of a channel for providing a stabilization rod to a rod receiving recess of a receiving part of the bone anchor, and a coupling portion, which is provided at a distal end of the elongate shaft portion and which is configured to be coupled to the receiving part. The coupling portion includes a first engagement portion for engaging a first engagement face of the receiving part and a second engagement portion for engaging a second engagement face of the receiving part. A spring element is provided at the coupling portion, the spring element exerting a compression force to urge the first and second engagement portions in mutually opposite directions towards each other and towards the corresponding first and second engagement faces along a longitudinal axis defined by the extension device and the receiving part when being coupled together.

21 Claims, 11 Drawing Sheets

(56) References Cited

U.S. PATENT DOCUMENTS

| | | | |
|---|---|---|---|
| 2003/0225408 A1* | 12/2003 | Nichols | A61B 17/7032 606/86 A |
| 2005/0085813 A1 | 4/2005 | Spitler et al. | |
| 2005/0149053 A1* | 7/2005 | Varieur | A61B 17/7091 606/104 |
| 2005/0192570 A1* | 9/2005 | Jackson | A61B 17/7011 606/914 |
| 2005/0261702 A1* | 11/2005 | Oribe | A61B 17/7086 606/103 |
| 2006/0079909 A1* | 4/2006 | Runco | A61B 17/7076 606/99 |
| 2006/0247658 A1* | 11/2006 | Pond, Jr. | A61B 17/7091 606/104 |
| 2007/0213714 A1* | 9/2007 | Justis | A61B 17/7002 606/86 A |
| 2007/0282337 A1* | 12/2007 | Garamszegi | A61B 17/7086 606/53 |
| 2009/0143828 A1* | 6/2009 | Stad | A61B 17/7085 606/86 A |
| 2009/0221877 A1* | 9/2009 | Woods | A61B 17/7085 600/201 |
| 2009/0222046 A1* | 9/2009 | Gorek | A61B 17/02 606/279 |
| 2009/0228053 A1* | 9/2009 | Kolb | A61B 17/7076 606/86 A |
| 2010/0114174 A1* | 5/2010 | Jones | A61B 17/7098 606/279 |
| 2011/0263945 A1* | 10/2011 | Peterson | A61B 17/0218 600/213 |
| 2012/0109208 A1* | 5/2012 | Justis | A61B 17/7032 606/264 |
| 2012/0191144 A1* | 7/2012 | Peultier | A61B 17/7086 606/86 A |
| 2012/0215266 A1* | 8/2012 | Jones | A61B 17/7086 606/86 A |
| 2012/0290011 A1* | 11/2012 | Justis | A61B 17/7085 606/278 |
| 2013/0096635 A1* | 4/2013 | Wall | A61B 17/7085 606/305 |
| 2013/0103096 A1* | 4/2013 | Miller | A61B 17/7032 606/305 |
| 2013/0245692 A1* | 9/2013 | Hayes | A61B 17/025 606/279 |
| 2013/0245702 A1* | 9/2013 | McBride | A61B 17/7076 606/305 |
| 2014/0052180 A1* | 2/2014 | Justis | A61B 17/7082 606/246 |
| 2014/0052187 A1* | 2/2014 | McBride | A61B 17/7085 606/264 |
| 2014/0052197 A1* | 2/2014 | McBride | A61B 17/7085 606/86 A |
| 2014/0236239 A1 | 8/2014 | Biedermann et al. | |
| 2014/0277137 A1* | 9/2014 | Stad | A61B 17/7076 606/246 |
| 2014/0277197 A1* | 9/2014 | Brown | A61B 17/7086 606/86 A |
| 2014/0277200 A1* | 9/2014 | Parker | A61B 17/7076 606/86 A |
| 2014/0316475 A1* | 10/2014 | Parikh | A61B 17/7083 606/86 A |
| 2014/0364912 A1* | 12/2014 | May | A61B 17/7043 606/253 |
| 2015/0051648 A1* | 2/2015 | May | A61B 17/7086 606/264 |
| 2015/0112397 A1* | 4/2015 | Petit | A61B 17/7076 606/86 A |
| 2015/0257798 A1* | 9/2015 | Biedermann | A61B 17/7076 606/86 A |
| 2015/0351810 A1* | 12/2015 | Lindner | A61B 17/7032 606/278 |
| 2016/0089188 A1* | 3/2016 | McBride, Jr. | A61B 17/7076 606/279 |
| 2016/0106480 A1* | 4/2016 | Zhou | A61B 17/7002 606/86 A |
| 2016/0113682 A1* | 4/2016 | Altarac | A61B 17/7085 606/265 |
| 2016/0206354 A1* | 7/2016 | Mladenov | A61B 17/7002 |
| 2016/0331420 A1* | 11/2016 | Dandanopoulos | A61B 17/708 |
| 2016/0354073 A1* | 12/2016 | Nel | A61B 17/02 |
| 2017/0100164 A1* | 4/2017 | Landry | A61B 17/708 |

FOREIGN PATENT DOCUMENTS

| | | |
|---|---|---|
| EP | 2 201 902 A1 | 6/2010 |
| EP | 2 201 903 A1 | 6/2010 |
| EP | 2 204 129 A1 | 7/2010 |
| EP | 2 221 013 A1 | 8/2010 |
| EP | 2 384 709 A1 | 11/2011 |

* cited by examiner

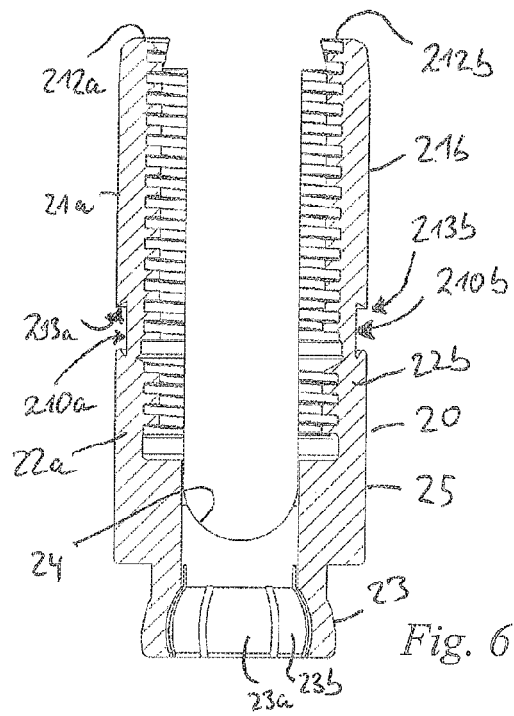
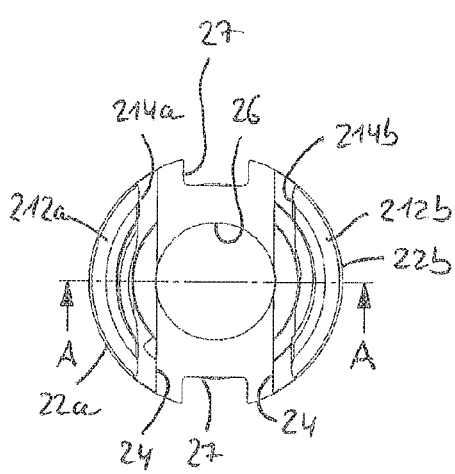
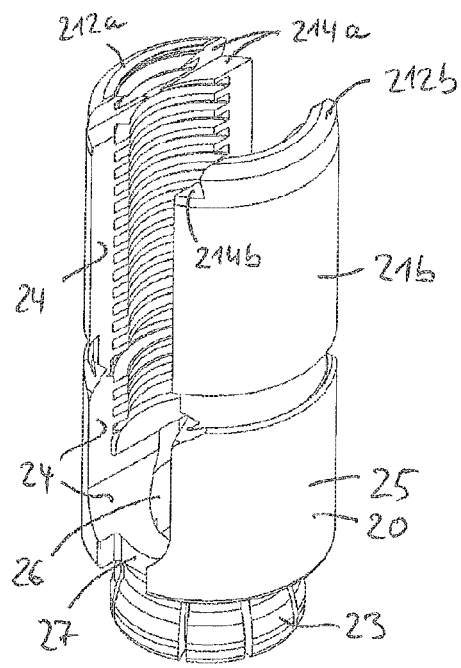
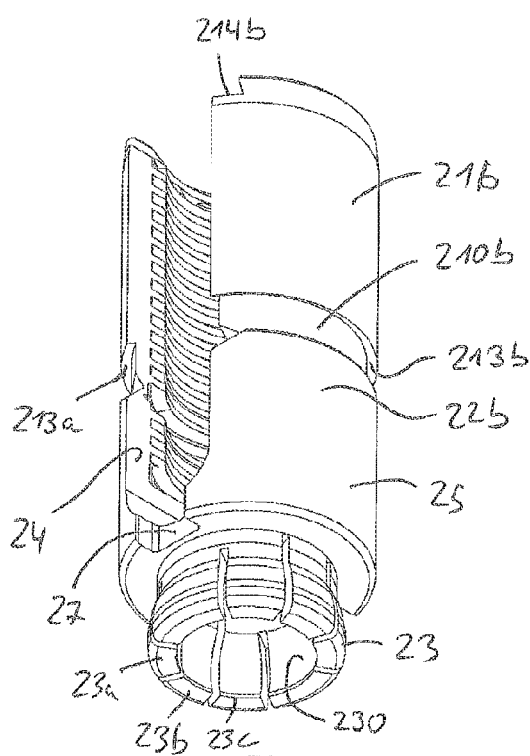
Fig. 6
Fig. 5
Fig. 7A
Fig. 7B

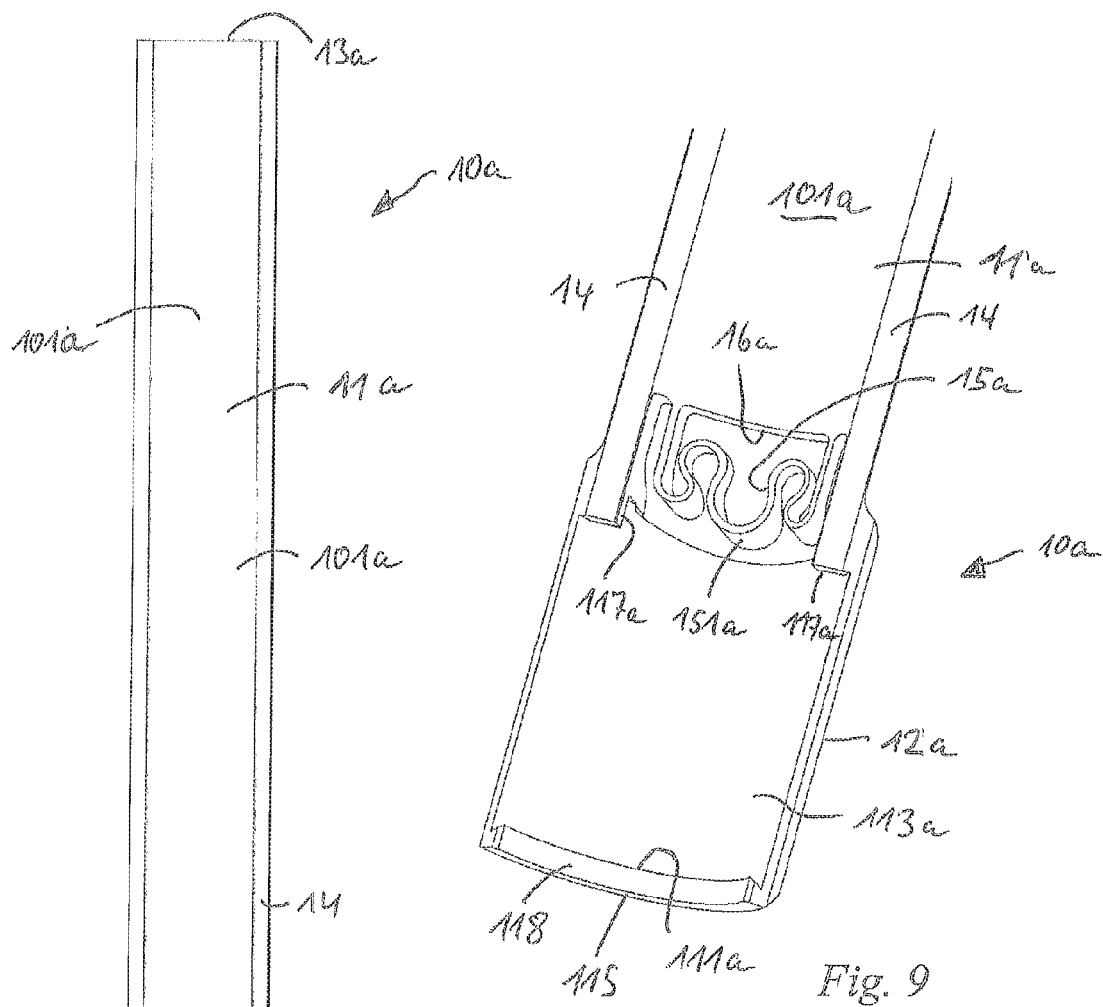

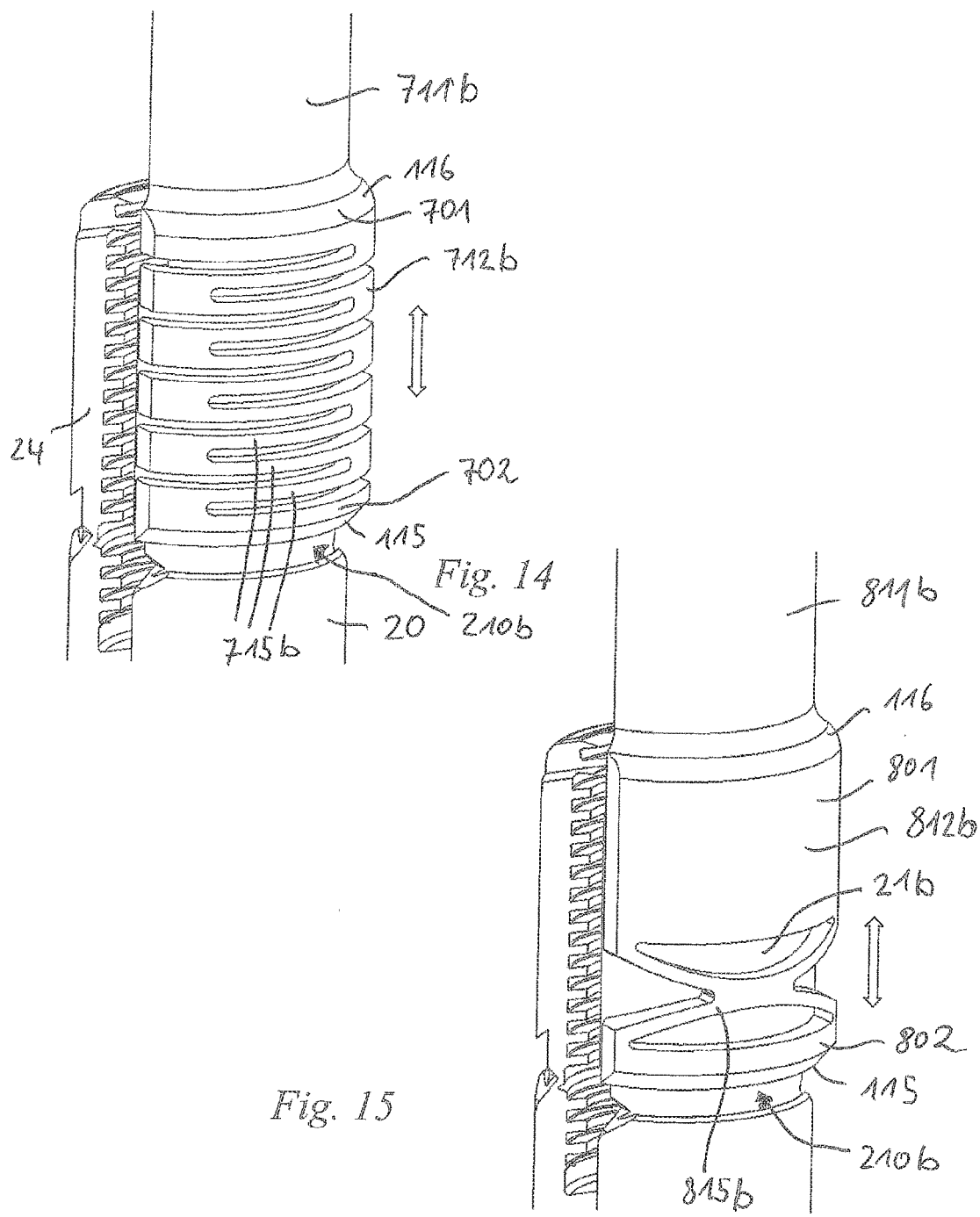

EXTENSION DEVICE FOR A BONE ANCHOR

CROSS-REFERENCE TO RELATED APPLICATIONS

The present application claims the benefit of U.S. Provisional Application Ser. No. 62/180,482, filed Jun. 16, 2015, the contents of which are hereby incorporated by reference in their entirety, and claims priority to European Patent Application EP 15 172 334.3, filed Jun. 16, 2015, the contents of which are hereby incorporated by reference in their entirety.

BACKGROUND

Field

The present disclosure relates to an extension device for a bone anchor, which includes at least one tab. The tab includes an elongate shaft portion that forms part of a channel for providing a stabilization rod to a recess of a receiving part of a bone anchor, and also includes a coupling portion, which is configured to be attached to the receiving part.

Description of the Related Art

Document US 2006/0247658 A1 discloses an apparatus for guiding a surgical implant to a bone anchor during surgery. The apparatus includes a bone anchor extender releasably attachable to the bone anchor, where the bone anchor extender clips onto a head of the bone anchor to assist in guiding the surgical implant to the bone anchor. The bone anchor extender includes a clip with a pair of raised tabs on opposite side portions of the clip. A medial portion and the corresponding side portions of the clip have a thickness allowing the side portions to elastically deform and/or bend in a lateral direction and then revert back to their original shape. The raised tabs have angled faces and retention edges which assist in guiding the extender onto the head and snap the clip to the bone anchor.

Document US 2005/0085813 A1 discloses a brace-screw assembly. The assembly is delivered along with an anchor extension device, or cannula, for anchoring in a vertebrae pedicle. The extension device has flexible fingers at the distal end and protrusions in the form of small pyramids are formed on the inside of these fingers. These pyramids fit into a tight mating relationship with mating structures of the screw assembly. To attach or release the extension device to the assembly, the fingers are caused to fly outward when the pyramids and mating structures leave their mated states.

SUMMARY

Particularly in minimally invasive surgery (MIS), it is desirable to perform tasks such as attaching a receiving part to a head of an implanted screw, supplying a rod to the receiving part, supplying a set screw for fixation of the rod and/or breaking-off extension tabs from legs of a receiving part using extension devices occupying less space, while improving the ease of performing the cited tasks, and facilitating the handling and reliability of the performed actions.

Embodiments of the present invention provide an extension device which addresses at least some of the above issues.

According to an aspect of the invention, the extension device includes at least one tab, for example two tabs, which each include an elongate shaft portion and a coupling portion. The coupling portion includes first and second engagement portions for engaging and coupling to respective engagement faces provided at a receiving part. A spring element is provided at the coupling portion to exert a compression force onto the receiving part to urge the engagement portions in mutually opposite directions towards each other. This compression force is oriented along a longitudinal axis associated with the extension device and also with the receiving part.

The spring element of the invention thus allows engaging respective engagement faces of the receiving part in substantially the same direction in which, for example, the receiving part is mounted to the tabs, and in which the receiving part is then transferred together with the tabs into a hole created in body tissue to attach the receiving part to the head of a bone anchor implanted in a bone, for example, a vertebra. In other words, the receiving part is coupled to the tab or tabs of the extension device in a form-fit manner without applying a circumstantial rotational movement. Since the spring element exerts the compression force in opposite directions, the engagement portions allow securely clamping of the receiving part by means of the one or more tabs.

Moreover, since no rotational movement needs to be performed to clamp the receiving part, the spring element allows the coupling portion to snap onto a receiving part in a longitudinal direction, which may yield a tactile response to the operator who assembles the extension device with the receiving part. In the case of extension devices known in the art, where an extension device is coupled to the receiving part using a rotational movement or by a lateral snapping movement, the tactile response may be of less quality, or hardly visible canting of the respective parts may occur, or in-situ attaching or releasing operations in MIS procedures may be hindered.

According to a further aspect of the invention, the spring element may, for example, be integrally formed with the extension device such that the number of parts may be reduced.

According to still a further aspect of the invention, the one or more tabs may be arranged to remove extension tab portions provided at the free ends of the legs of a receiving part, i.e., to break-off these extension tab portions once the tabs of the device have been used to guide and load the receiving part to a head of an implanted screw. Such extension tab portions are commonly used to temporarily provide an extended inner thread in the receiving part for the purpose of guiding a set screw to the receiving part to fix a stabilization rod provided in a rod receiving channel of the receiving part.

If two tabs are used with the extension device, a channel is provided for delivering a stabilization rod to the rod receiving channel of the receiving part. In one embodiment, the tabs may be separate parts, but in another embodiment, the tabs may also be coupled to each other in a sleeve-like fashion.

According to a further aspect, the extension device includes two separate long tabs. Such an extension device may advantageously be applied to known bone anchor assemblies such as disclosed in documents EP 2 022 423 A1, EP 2 191 780 A1, EP 2 201 902 A1, EP 2 201 903 A1, EP 2 204 129 A1, EP 2 221 013 A1, or EP 2 384 709 A1, all documents by Applicant, among others. The bone anchor assemblies disclosed in these documents are particularly advantageous in MIS procedures. One specific embodiment is explained below in the detailed description, which is very similar to the function and use of the bone anchor assemblies disclosed in the above documents. The contents of the documents are thus incorporated herein by reference. One main difference of the instant embodiments with respect to those disclosed in the above listed documents is found, however, in that removable extension tab portions are additionally provided at the free ends of the legs of the receiving part.

According to a further aspect, the invention also relates to a combination of the extension device with the bone anchor assembly.

BRIEF DESCRIPTION OF THE DRAWINGS

Aspects and advantages of the invention will be readily understood by the following detailed description of embodiments taken in conjunction with the accompanying drawings. Therein:

FIG. 5 shows a top view of the receiving part of the bone anchor assembly according to the first embodiment;

FIG. 6 shows a cross-sectional view of the receiving part, the cross-section taken along line A-A in FIG. 5;

FIG. 7A shows a top perspective view of the receiving part shown in FIG. 6;

FIG. 7B shows a bottom perspective view of the receiving part shown in FIG. 6;

FIG. 8 shows a front view of one tab of the extension device according to the first embodiment;

FIG. 9 shows an enlarged perspective view of the coupling portion of the tab of the extension device shown in FIG. 8;

FIG. 14 shows in an enlarged perspective view a coupling portion of an extension device coupled to a receiving part according to a fourth embodiment of the invention;

FIG. 15 shows in an enlarged perspective view a coupling portion of an extension device coupled to a receiving part according to a fifth embodiment of the invention;

DETAILED DESCRIPTION

Figures 1, 2:
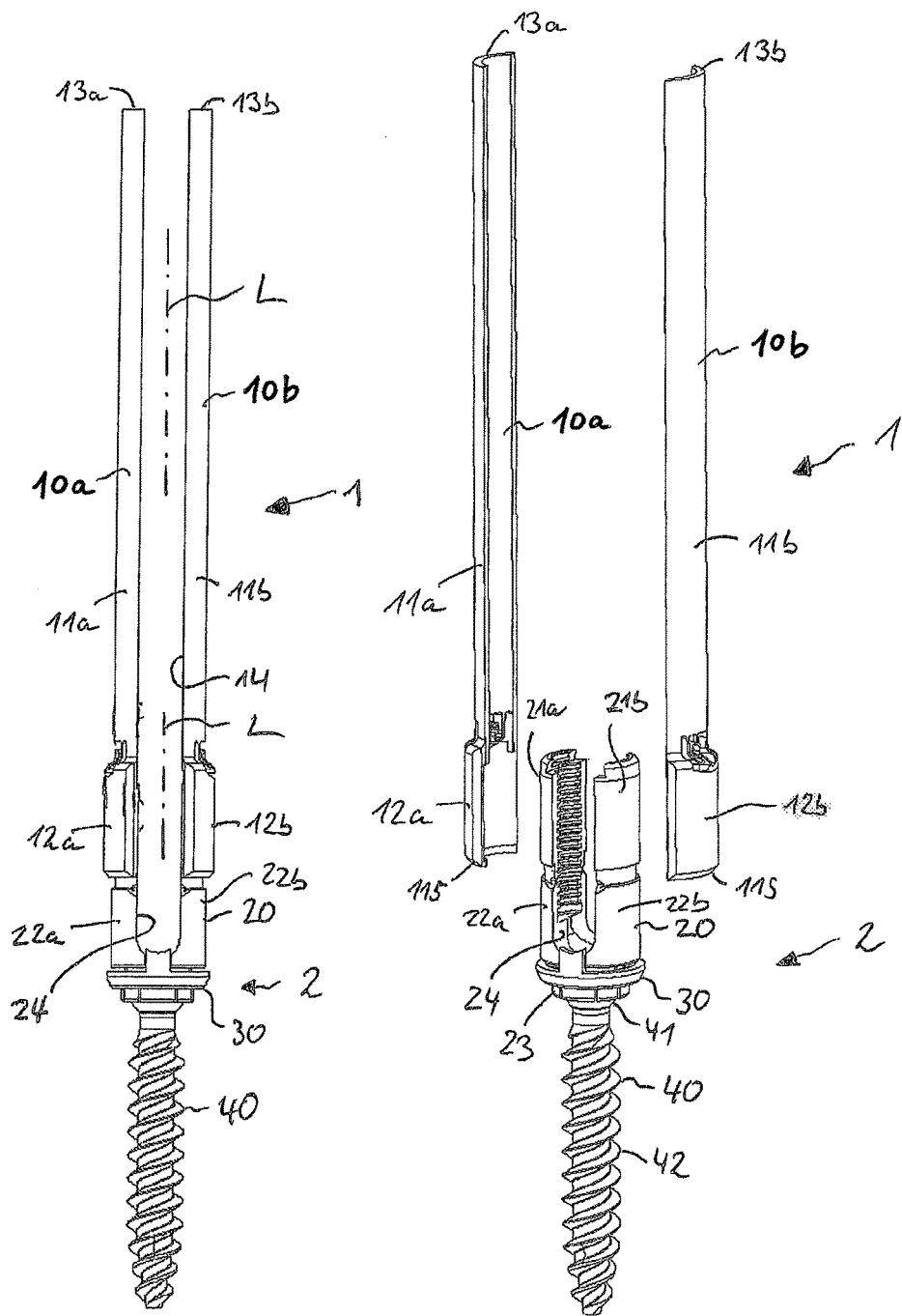
FIG. 1 shows a side view of an extension device coupled to a bone anchor assembly according to a first embodiment of the invention.
FIG. 2 shows a perspective view of the extension device and the bone anchor assembly of FIG. 1 with the tabs of the extension device detached from the receiving part of the bone anchor assembly according to the first embodiment.

An extension device 1 according to a first embodiment of the present invention is described with reference to FIGS. 1 through 11H. FIG. 1 depicts an overview of the extension device 1, which is coupled to a bone anchor assembly 2, whereas FIG. 2 depicts a partially exploded view of FIG. 1. The extension device 1 includes two tabs 10a, 10b, which are formed as separate parts in this embodiment, and which are each arranged to be respectively coupled to one leg 22a, 22b of a receiving part 20 of the bone anchor assembly 2. More specifically, each of the tabs 10a, 10b has an elongate shaft portion 11a, 11b, and a coupling portion 12a, 12b, respectively, where the coupling portions 12a, 12b are arranged to be coupled to removable extension tab portions 21a, 21b of the receiving part 20 provided at the legs 22a, 22b. The elongate shaft portions 11a, 11b and the coupling portions 12a, 12b are integrally formed with respect to each of tabs 10a, 10b.

The elongate shaft portions 11a, 11b of tabs 10a, 10b include a tubular segment-shape and are provided with inner cylindrical wall surfaces 101a, 101b and outer cylindrical wall surfaces 102a, 102b, as becomes apparent from FIGS. 3-4 and 8-10b. The cylindrical inner and outer wall surfaces 101a, 101b, 102a, 102b each define a tubular segment. The tube-shaped cylinder segments thereby define a longitudinal axis L as shown in FIG. 1. When the tabs 10a, 10b are mounted to the receiving part 20 of the bone anchor assembly 2, the longitudinal axis L coincides with a longitudinal axis of the receiving part 20.

The coupling portions 12a, 12b of tabs 10a, 10b similarly include a tubular segment-shape having cylindrical inner wall surfaces 113a, 113b and cylindrical outer wall surfaces 112a, 112b extending between ends 115, 116 of the coupling portions 12a, 12b. This tubular segment-shape as well as the cylindrical wall surfaces 112a, 112b, 113a, 113b also define a longitudinal axis which coincides with longitudinal axis L defined by the elongate shaft portions 11a, 11b.

Figure 3:
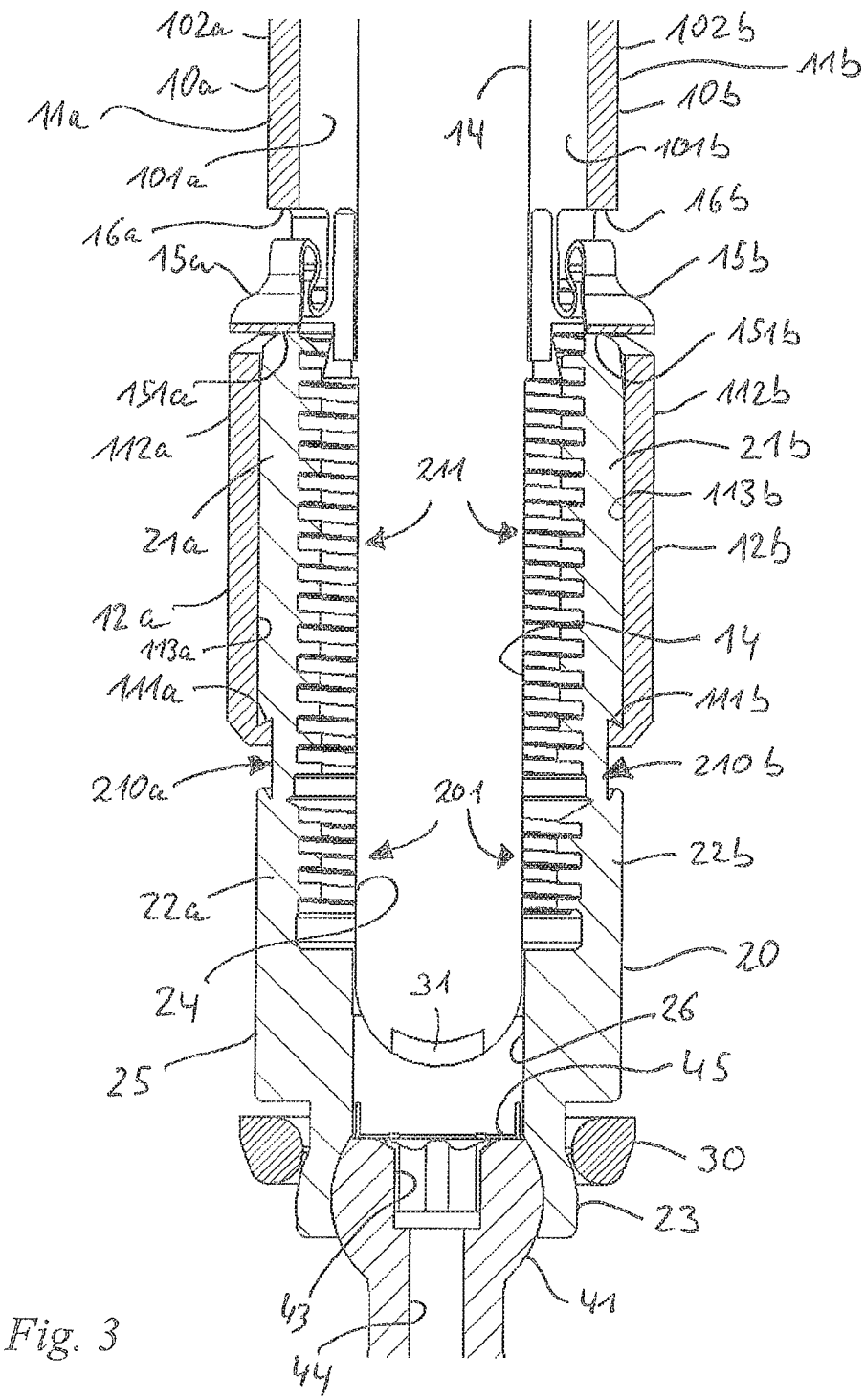
FIG. 3 shows a cross-sectional view of the extension device and bone anchor assembly of FIGS. 1 and 2.

However, the tubular segment-shape and the inner and outer wall surfaces 112a, 112b, 113a, 113b of the coupling portions 12a, 12b are radially offset from the central longitudinal axis L as compared with the tubular segment-shape and inner and outer wall surfaces 101a, 101b, 102a, 102b of elongate shaft portions 11a, 11b, as can be seen particularly in FIG. 3. In other words, radii of the walls of the coupling portion 12a, 12b as measured from the longitudinal central axis L are larger than corresponding radii of the walls of the elongate shaft portions 11a, 11b. This allow the coupling portions 12a, 12b to encompass and be closely attached to cylindrical wall surfaces provided at the legs 22a, 22b of the receiving part 20 and particularly at the removable extension tab portions 21a, 21b thereof.

Consequently, as can be seen particularly in FIG. 3, when the tabs 10a, 10b are coupled and attached to the receiving part 20, the inner wall surfaces 101a, 101b form a bore which is substantially flush with an inner bore formed in the receiving part 20, where the inner bore of the receiving part 20 includes the outer diameters of the inner threads 211, 201, i.e., the thread roots of the flat thread shown. This feature allows a set screw to advance through the tabs 10a, 10b of the extension device 1, using a screwing tool (not shown), up to the start of the inner thread 211, and then subsequently screwing-in the set screw through the inner threads 211 and 201.

Figure 4:
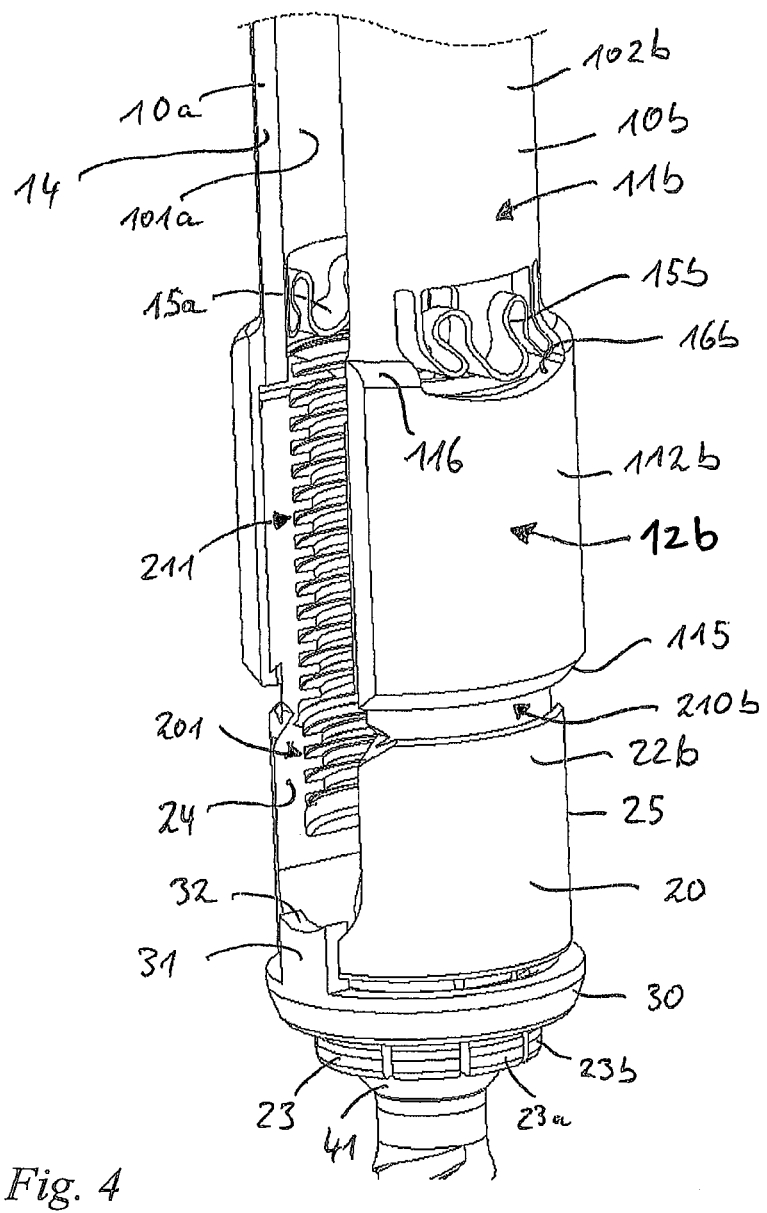
FIG. 4 shows an enlarged perspective view of the extension device coupled to the receiving part of the bone anchor assembly according to the first embodiment.

Still further, edges of the elongate shaft portions 11a, 11b define a channel 14 when both tabs 10a, 10b are mounted to the receiving part 20, as can be seen from FIGS. 1, 3 and 4. This channel 14 has the same width as a U-shaped rod receiving channel 24 formed in the receiving part 20, which defines respective legs 22a, 22b thereof. The channel 14, defined by tabs 10a, 10b, is also flush with the rod receiving channel 24 formed at the receiving part 20. This allows a stabilizing rod to be firmly and reliably guided to the rod receiving channel 24 of the receiving part 20 from the channel 14 of the tabs 10a, 10b.

The bone anchor assembly 2 includes the receiving part 20, a locking ring 30, and a bone anchoring element 40, as can be seen in FIGS. 1 and 2. The receiving part 20 has a first substantially cylindrical section 25, which includes the above mentioned inner bore, the U-shaped rod receiving channel 24, and the legs 22a, 22b, as can be seen in FIGS. 5 through 7B. The legs 22a, 22b extend beyond predetermined breaking points 210a, 210b up to first engagement faces 212a, 212b provided at free ends of the legs 22a, 22b, respectively. The portions of the legs 22a, 22b which may be broken-off via breaking points 210a, 210b are denoted herein as the removable extension tab portions 21a, 21b. In this embodiment, the tabs 10a, 10b are coupled only to the removable extension tab portions 21a, 21b to facilitate breaking-off the removable extension tab portions 21a, 21b.

In other embodiments of the invention, the coupling portions of the tabs may be coupled to portions of the legs of a receiving part which are not configured to be removed.

The receiving part 20 further includes a clamping portion 23, which is arranged to receive and clamp a head 41 of the bone anchoring element 40. For this purpose, a partially spherical accommodation space 230 (see FIG. 7B) is provided and resiliently deflectable tabs 23a, 23b, 23c are formed to allow introduction of the head 41 therein from a bottom side of the receiving part 20. In such a state, prior to final fixation or locking, the head 41 of the anchoring element 40 may be held in position by friction.

Locking of the head 41 is enabled by adjusting locking ring 30 to press against the clamping portion 23. As shown in FIGS. 3 and 4, the locking ring 30 has two protrusions 31 extending through respective apertures 27 of the first section 25 of the receiving part 20 and into the U-shaped rod receiving channel 24. When a stabilization rod (not shown) is inserted and received on a rod receiving face 32 of the protrusions 31, the locking ring 30 is urged downwards towards the bottom side of the receiving part 20, where an inner rounded or tapered face of the locking ring 30 engages the outer tapered faces of the tabs 23a, 23b, 23c of the receiving part 20, which in turn deflect inwards and firmly clamp the head 41 of the bone anchoring element 40. The force which urges the locking ring 30 towards the bottom side of the receiving part 20 originates from the set screw threaded into inner threads 211, 201 (set screw not shown in the drawings).

The bone anchoring element 40 includes the spherical head 41 and a threaded portion 42, as can be seen in FIG. 2. As noted above, the anchoring element 40 is loaded to the receiving part 20 from the bottom thereof (i.e., the receiving part is a "bottom loader").

Details of the features related to the coupling of the tabs 10a, 10b to the receiving part 20 are explained with particular reference to FIGS. 3, 4 and 8-10b. The coupling portions 12a, 12b include the tubular segment-shape which extends from the distal end 115 up to a proximal end 116 of the coupling portions 12a, 12b. The terms "proximal" and "distal" as used herein are defined from the operator's or surgeon's view. At the proximal end 116, apertures 16a, 16b are formed through the tabs 10a, 10b, respectively, within which meandering spring elements 15a, 15b are each supported and integrally connected with the tabs 10a, 10b at two ends.

Figures 10A, 10B:
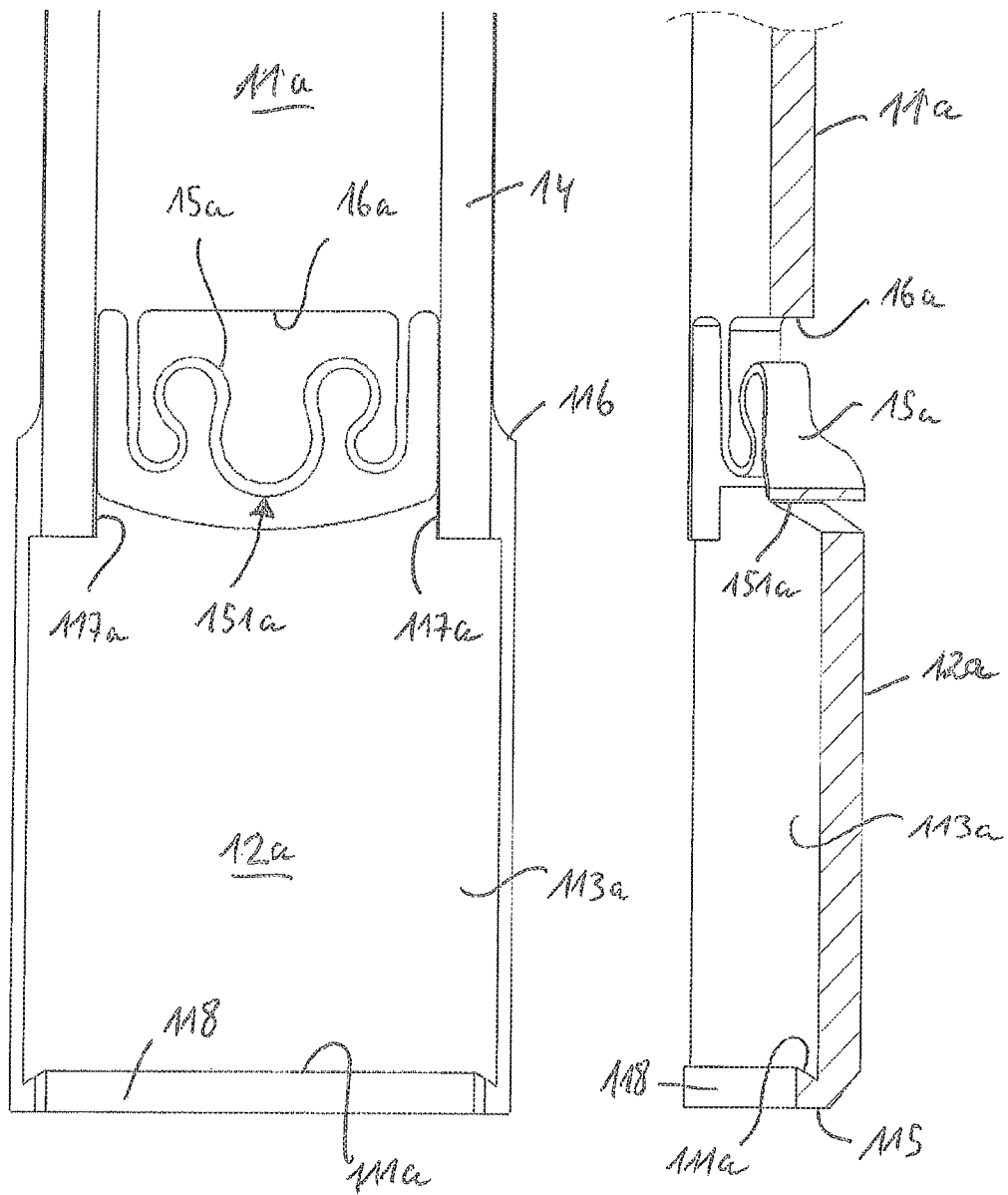
FIG. 10A shows an enlarged front view of the coupling portion shown in FIG. 9.
FIG. 10B shows a cross-sectional side view of the coupling portion shown in FIG. 10A.

The meandering spring elements 15a, 15b are arranged to be resiliently deflectable particularly in a direction along the longitudinal axis L in view of its construction as a meandering thin metal strip. Each of the spring elements 15a, 15b also has a bulgy shape, where one bulge provides an abutment face, or first engagement portion 1512, 151b which may abut the first engagement face 212a, 212b provided at the free ends of legs 22a, 22b, respectively. For this purpose, the spring element 15a, 15b protrudes inwards with respect to the inner wall surfaces 113a, 113b of the coupling portions 12a, 12b, as can be seen in FIG. 10B. In this manner, the spring elements 15a, 15b may exert a force onto the first engagement faces 212a, 212b of the receiving part 20 when an abutment is achieved during a coupling operation as will be described below.

At the distal end 115 of coupling portions 12a, 12b, second engagement portions 111a, 111b are provided. The second engagement portions 111a, 111b are formed by inner annular segment-shaped protrusions 118 which extend along the edge of the distal end 115. It may be noted that one or more single hooks may also be provided. The protrusion 118 has an upper inclined face that slopes outwardly and forms the second engagement portions 111a, 111b. As can particularly be seen in FIGS. 3, 6 and 7B, the inclined engagement portions 111a, 111b are arranged to mate with complementarily inclined second engagement faces 213a, 213b of the legs 22a, 22b of the receiving part 20 in a form-fit manner. The outwardly sloping engagement faces 213a, 213b of the legs 22a, 22b provide a reliable form-fit connection, which prevent loosening when larger forces are exerted on the tabs 10a, 10b. Also, the second engagement faces 213a, 213b are provided at the legs 22a, 22b of the receiving part 20, or more specifically at the bottom ends of the removable extension tab portions 21a, 21b adjacent the predetermined breaking points 210a, 210b, and extend in an annular manner around the cylindrical segment-shaped surfaces thereof.

In an uncoupled, relaxed state of the tabs 10a, 10b, a distance between the first engagement portions 151a, 151b and the second engagement portions 111a, 111b is less than a distance between the first engagement faces 212a, 212b and the second engagement faces 213a, 213b of the legs 22a, 22b, respectively. As a consequence, when the tabs 10a, 10b are coupled to the receiving part 20, the spring elements 15a, 15b exert a biasing force via first engagement portions 151a, 151b onto the first engagement faces 212a, 212b in a direction along the longitudinal axis L. In turn, the receiving part is urged downwards and the second engagement faces 213a, 213b are urged against the second engagement portions 111a, 111b, which results in a firm clamping of the receiving part 20. Also, the spring elements 15a, 15b exert an upwardly directed pulling force onto the coupling portions 12a, 12b, which urges the second engagement portions 111a, 111b against the second engagement faces 213a, 213b in a direction along the longitudinal axis L.

In other words, the spring elements 15a, 15b exert a compression or tensile force on both the first and second engagement portions 151a, 151b, 111a, 111b of the tabs 10a, 10b directed along the longitudinal axis L and towards each other and against the first and second engagement faces 212a, 212b, 213a, 213b of the legs 22a, 22b of the receiving part 20.

In order to prevent rotation of the receiving part 20 with respect to the extension device 1, each tab 10a, 10b has a protrusion 117a, 117b which is configured to mate with a corresponding recess 214a, 214b provided adjacent the free ends of the legs 22a, 22b, or of the removable extension tab portions 21a, 21b, of the receiving part 20. In alternative embodiments, instead of protrusions 117a, 117b, recesses may also be provided at the side of the tabs 10a, 10b, while protrusions may be provided at the side of the receiving part 20, in order to prevent rotation of the parts with respect to each other.

The protrusions 117a, 117b, adjacent the proximal end 116 and adjacent the spring elements 15a, 15b, allow an improved form-fit connection between the tabs 10a, 10b and the receiving part 20. Thereby, the spring elements 15a, 15b allow the form-fit connection to be maintained in a resilient manner.

A method of coupling the tabs 10a, 10b to the receiving part 20 is described with reference to a sequence of steps illustrated in FIGS. 11A-11H. The illustrated steps of assembling the tabs 10a, 10b and the receiving part 20 are preferably performed outside the human body.

Figure 11A:
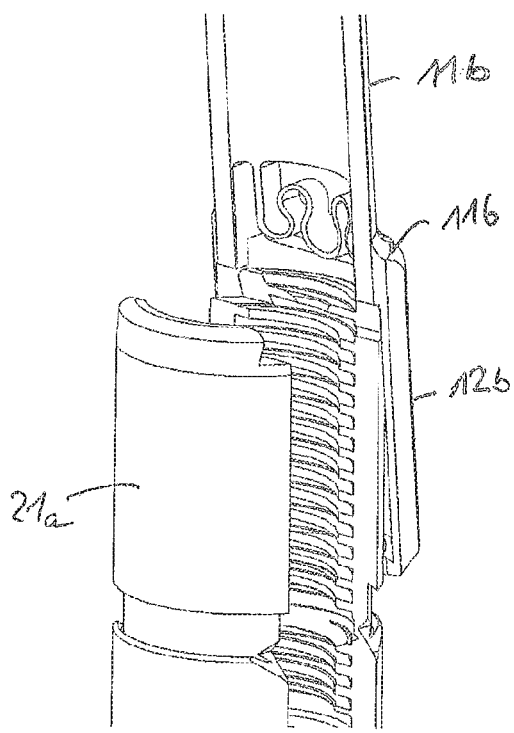
FIG. 11A shows in a perspective view a first step of a method of coupling a tab of the extension device to a removable extension tab portion of a receiving part according to the first embodiment.
Figure 11B:
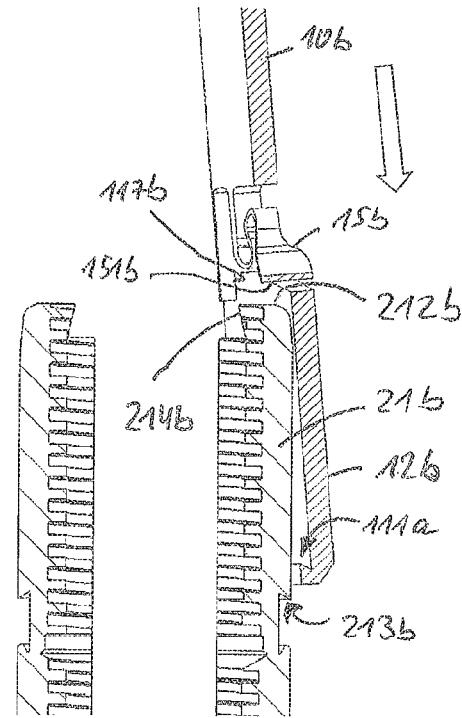
FIG. 11B shows a cross-sectional view of the step in FIG. 11A.

A first step is shown in FIG. 11A and FIG. 11B. As indicated by the arrow in FIG. 11B, one tab 10b is slid onto the removable extension tab portion 21b of the receiving part 20 in an inclined posture substantially in a direction along the longitudinal axis L to allow the first engagement portion 151b of spring element 15b to contact the first engagement face 212b at the free end of leg 22b.

Figure 11C:
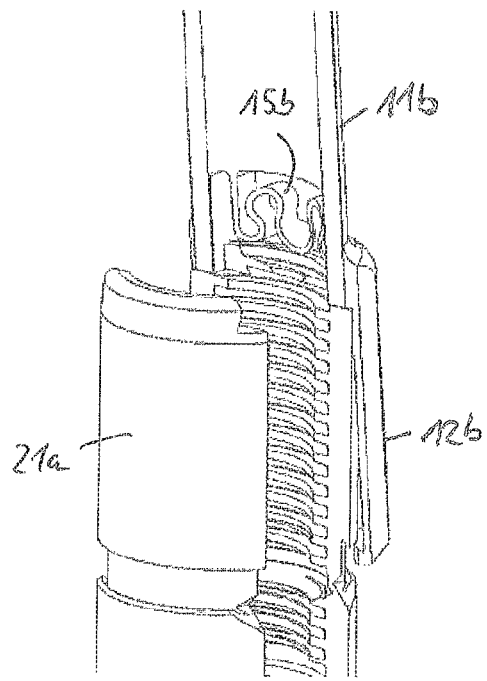
FIG. 11C shows a second step of a method for coupling the extension device tab to a receiving part in a perspective view according to the first embodiment.
Figure 11D:
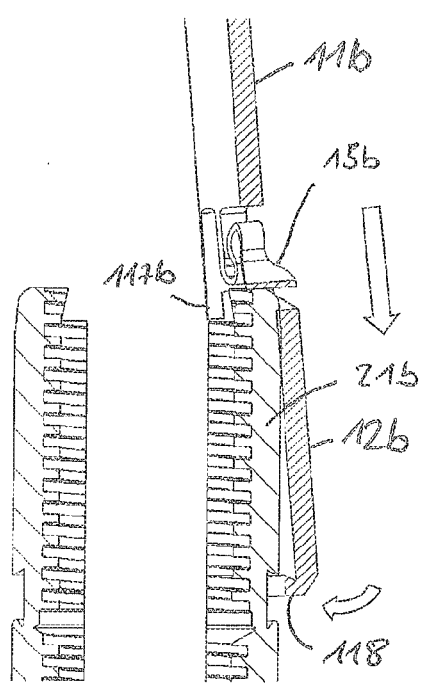
FIG. 11D shows a cross-sectional view of the step in FIG. 11C.

As can be seen in the second step of the method shown in FIG. 11C and FIG. 11D, the protrusion 118 at the distal end of coupling portion 12b slides along the outer cylindrical surface of the removable extension tab portion 21b, whereby the spring element 15b is now tensioned due to the abutment with the first engagement face 212b. At this instant, the protrusion 117b of the coupling portion 12b also mates into the recess 214b of the receiving part 20 in a form-fit manner.

Figure 11E:
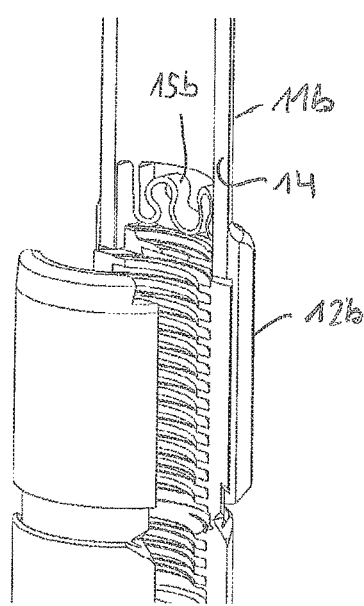
FIG. 11E shows a third step of a method of coupling an extension device tab to a receiving part according to the first embodiment in an enlarged perspective view.
Figure 11F:
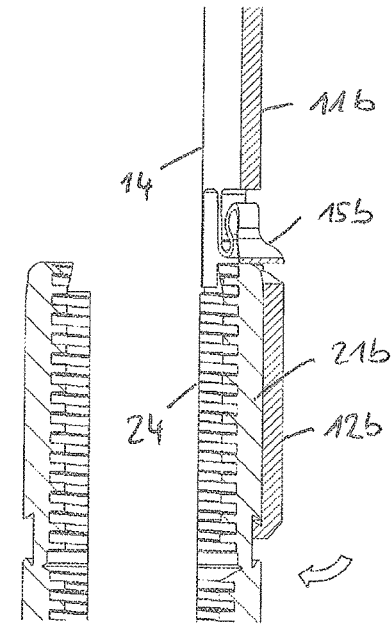
FIG. 11F shows a cross-sectional view of the step in FIG. 11E.

As shown in the third step of the method shown in FIGS. 11E and F, once the spring element 15b is sufficiently tensioned, the protrusion 118 may snap or latch behind second engagement face 213b as indicated by the arrow in FIGS. 11D and 11F. Thereby, a small force is applied to align the longitudinal axes L of the receiving part 20 and the tab 10b. At this instant, after performing the third step of latching-in the protrusion 118, a state shown in FIGS. 11E and 11F is achieved.

Figure 11G:
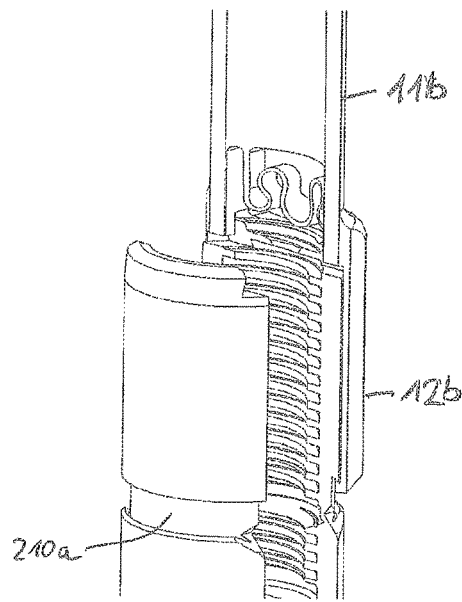
FIG. 11G shows a fourth step of a method of coupling an extension device tab to a receiving part according to the first embodiment in an enlarged view.
Figure 11H:
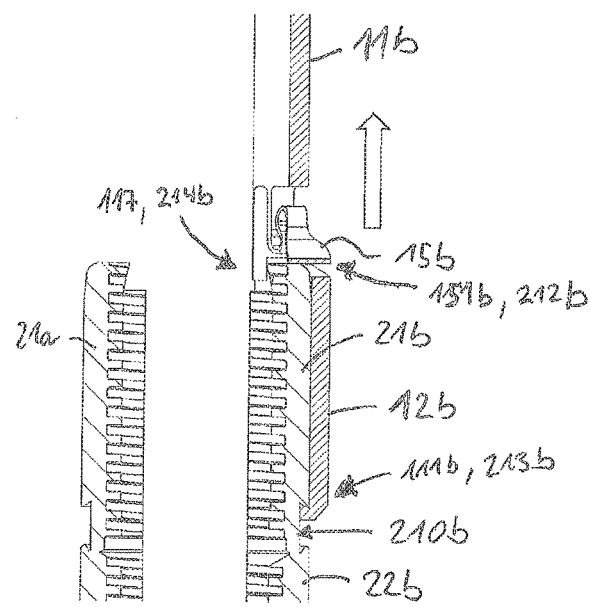
FIG. 11H shows a cross-sectional view of the step in FIG. 11G.

In a fourth step of a method of coupling the tab 10b to the receiving part 20 shown in FIGS. 11G and 11H, a downward force exerted onto the tab 10a and tensioning the spring element 15b against the first engagement face 212b is released as indicated by the upward arrow. As a consequence, the coupling portion 12b moves slightly upward and the second engagement portion 111b of the coupling portion 12b now engages the second engagement face 213b of the receiving part 20, while the form-fit connection between the protrusion 117b and the recess 114b is maintained as well as the pressure contact between the first engagement portion 151b and the first engagement face 212b.

As indicated in FIGS. 11G and 11GH, a coupled state between the tab 10b and the receiving part 20 is achieved and the second tab 10a may be coupled to the receiving part 20 in a similar manner with respect to the other removable extension tab portion 21a thereof. Other operations may be subsequently performed, such as guiding the coupled receiving part 20 to an implant hole and to a head of an anchoring element implanted in a bone, guiding a stabilization rod (not shown) through the channel 14 of the tabs 10a, 10b to the rod receiving channel 24 of the receiving part 20, and/or guiding a set screw through the inner bore between tabs 10a, 10b, etc., and screwing-in the set screw to fixate the stabilization rod in the receiving part 20. Thereafter, the tabs 10a and 10b may be cautiously pulled, for example, at their top ends 13a, 13b, away from the longitudinal axis L to break-off the removable extension tab portions 21a, 21b of the receiving part 20 coupled to the coupling portions 12a, 12b of the tabs 10a, 10b at the respective predetermined breaking points 210a, 210b. Due to the form-fit connection between the tabs 10a, 10b and the extension tab portions 21a, 21b, the removed extension tab portions 21a, 21b may safely be withdrawn from the implant hole in the body tissue.

Alternative embodiments are explained with respect to FIGS. 12-15. Same parts are denoted with same numerals and repeated descriptions thereof will be omitted in the following in this and the further embodiments.

Figure 12:
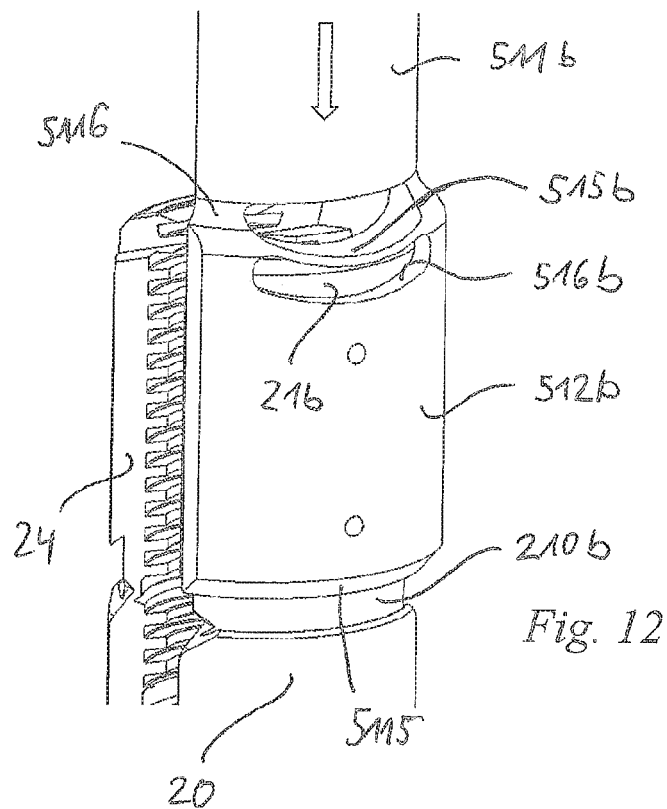
FIG. 12 shows in an enlarged perspective view a coupling portion of an extension device coupled to a receiving part according to a second embodiment of the invention.

A second embodiment is shown in FIG. 12. The second embodiment differs from the first embodiment in that instead of a meander spring element 15a, 15b, the spring element 515b has a function of a leaf spring which may abut a corresponding first engagement face 212b of the receiving part 20. Similar to the first embodiment, an aperture 516b is formed, through which the spring element 515b extends from one end to the other. The leaf spring element 515b is integrally formed with the coupling portion 512b. Also, the spring element 515b, including the first engagement portion and the aperture 516b, is formed adjacent the proximal end 5116 of the coupling portion 512b. The second engagement portion (not shown) is similar or identical to that of the first embodiment, and is provided adjacent the distal end 5115 of the coupling portion 512b.

Figure 13:
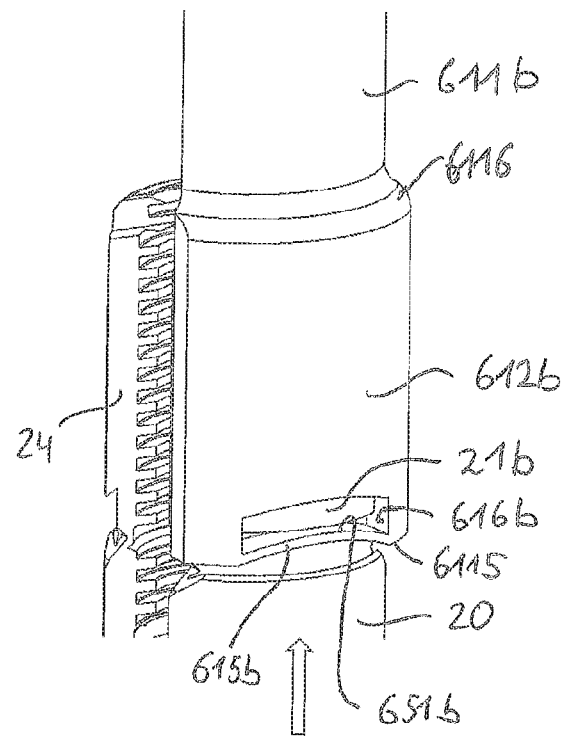
FIG. 13 shows in an enlarged perspective view a coupling portion of an extension device coupled to a receiving part according to a third embodiment of the invention.

A third embodiment is shown in FIG. 13. The third embodiment differs from the first and second embodiments in that a spring element 615b, which is formed as a leaf spring, is provided adjacent the distal end 6115 of the coupling portion 612b. Accordingly, a face of the spring element 615b oriented towards the proximal end 6116 of the coupling portion 612b functions as a first engagement portion 651b and engages the engagement face 213b of the receiving part 20 as in the previous embodiments. However, the biasing force in this embodiment is exerted in a proximal direction towards the proximal end 6116. The coupling portion 612b then has at the proximal end 6116 a corresponding second engagement portion, which may be formed, similar to the first embodiment, as an annular protrusion having an inclined face, which engages with a corresponding engagement face of the receiving part 20 in a form-fit manner. As indicated by the arrow in FIG. 13, in a method of coupling the tab to the receiving part 20, the contact between the spring element 615b and the first engagement face of the removable extension tab portion has to be established first, and the spring element 615*b* is tensioned by an upward movement.

It is to be noted that also in the second and third embodiments, protrusions or recesses are provided at the side of the tabs in order to prevent rotation between the tabs and the receiving part as in the first embodiment.

A fourth embodiment is shown in FIG. 14. This embodiment differs from the previous embodiments in that the coupling portion 712*b* includes two distinct rigid sections 701, 702, which are not directly connected with each other, but are connected via meandering spring element 715*b*. Each of the distinct sections 701, 702 is provided at the proximal and distal ends 116, 115 of the coupling portion 712*b*, respectively, and includes respective engagement portions (not shown) for engaging the receiving part 20 in a form-fit manner. FIG. 14 shows the coupled state. In the coupled state, the spring element 715*b* is tensioned. A method of coupling the tab to a receiving part is similar to that as explained with reference to FIG. 13, i.e., the distal end 115 and its respective engagement portion is coupled first to the receiving part 20.

The fifth embodiment is explained with reference to FIG. 15. The fifth embodiment is similar to the fourth embodiment, with the only difference is that instead of a meandering spring 715*b*, a double leaf spring or partial wave spring element 815*b* is provided. Nevertheless, the coupling portion 812*b* has, as in the fourth embodiment, a first distinct section 801 and a second distinct section 802 provided at the proximal and distal ends 116, 115, respectively. Also the function is the same as explained with reference to FIG. 14.

Figures 16A, 16B:
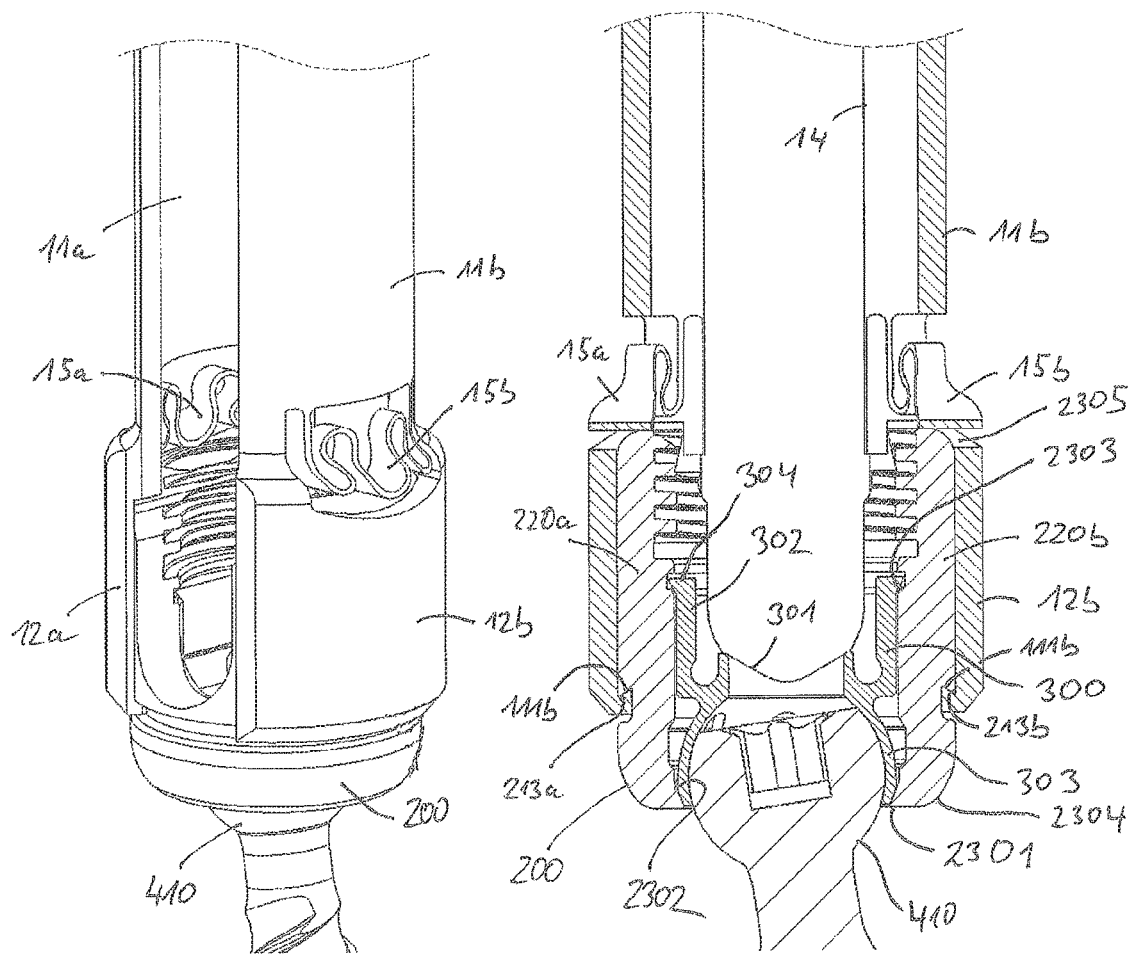
FIG. 16A shows in an enlarged perspective view a coupling portion of an extension device coupled to a receiving part according to a sixth embodiment of the invention.
FIG. 16B shows a cross sectional view of FIG. 16A.

A sixth embodiment is explained with reference to FIGS. 16A, 16B. Therein, the extension device 1 is identical or at least similar to that of the first embodiment. However, a receiving part 200 is used for coupling with the extension device 1, which has legs 220*a*, 220*b* not including removable extension tab portions, which is different from the previous embodiments. Rather, first and second engagement faces 213*a*, 213*b* are formed at the receiving part 200 in a portion adjacent a bottom end 2304 thereof to allow coupling portions 12*a*, 12*b* of extension device 1 to encompass the legs 220*a*, 220*b* and to allow first and second engagement portions 111*a*, 111*b* to engage the first and second engagement faces 213*a*, 213*b* of receiving part 200. A form-fit connection is achieved as in the previous embodiments by providing a protrusion 117*a*, 117*b* or recess provided adjacent a corresponding end 116 of the coupling portion 12*a*, 12*b* and a matching recess 214*a*, 214*b* or protrusion at a top end 2305 of the receiving part (not shown in FIGS. 16A, 16B).

In this sixth embodiment, the tabs 10*a*, 10*b* are not used to remove a removable extension tab portion (nevertheless, it is also possible that these were present before and have been broken away in a previous step). Rather, the device is configured to engage and guide a receiving part to an implantation site, preferably in MIS procedures. As in the previous embodiments, the receiving part 200 is designed to be top-loaded onto a head 410 of the bone anchoring element, which is, for example, anchored in a bone when the receiving part 200 is applied.

As further shown in this non-limiting example in the sixth embodiment, the receiving part 200 has a locking element 300 with arms 302 having protrusions 304 at their respective tips, a flexible section 303 for receiving and clamping the head 410, and a V-shaped groove for receiving stabilization rods having different diameters. The locking element 300 is received in an internal bore of the receiving part 200 which is provided with an annular recess 2303 into which the protrusions 304 may latch to create a pre-locked state, where the locking element 300 is prevented from being removed from the internal bore.

At the same time, the flexible section 303 encompassing the head 410 is held at least partially in a narrowing portion 2302 of opening 2301 at the bottom end 2304 of the receiving part 200, thereby preventing the head 410 from leaving the bottom opening 2301 and exerting a frictional force onto the head 410 to maintain a desired angular position of the head 410 of an anchoring element relative to the receiving part 200. Details of use of a similar locking element and its advantages may for example be found in document US 2014/0236239 A1, by Applicant, which is incorporated herein by reference in its entirety.

In the above embodiments, the tabs 10*a*, 10*b* of the extension device 1 may be formed from biocompatible metals such as stainless steel, titanium alloys, or the like as known in the art. Sufficiently stable plastic materials may also be used.

Various modifications may be made to the embodiments illustrated above, and persons skilled in the art will readily recognize those modifications as being part of the invention.

For example, in the above embodiments, a form-fit connection has been described as a combination of the first engagement portion provided at a spring element and a protrusion or recess provided adjacent a corresponding end of the coupling portion. However, the protrusion or recess preventing rotation of the tabs with respect to the receiving part may be combined with the spring element, or may be even provided at another location of the coupling element. For example, rotation may also be prevented by a specific shape of the inner wall of the coupling portion, which departs from a simple cylindrical surface, but which mates with a correspondingly shaped outer surface of the legs or removable extension tab portions.

In the above embodiments, the second engagement portion was described as an annular segment-shaped protrusion at the inner wall surface of the coupling portion. However, the second engagement portion may also refer to a protrusion having any other shape. It is also possible that the second engagement portion is itself provided on a second spring element.

In the above embodiments, the spring elements are described as parts integrally formed with the coupling portion. However, in alternative embodiments, the spring elements may also, be embodied as separate parts. Similarly, the coupling elements may be separate from the elongate shaft portions while being detachably connected.

Further, the spring elements may be formed from other materials than metals, for example resilient polymer materials.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. An extension device system comprising:
  a receiving part of a bone anchor, the receiving part comprising two legs defining a channel for receiving a rod, wherein each leg includes a first engagement face and a second engagement face; and
  at least one tab comprising:
    an elongate shaft portion that forms part of a channel for guiding surgical implants to the bone anchor; and a coupling portion provided at a distal end of the elongate shaft portion, wherein the coupling portion includes a first end, a second end, a first engagement portion adjacent the first end configured to engage the first engagement face of the receiving part, and a second engagement portion adjacent the second end configured to engage the second engagement face of the receiving part, wherein the first engagement portion is axially between the second engagement portion and the elongate shaft portion, wherein a spring element is provided at the coupling portion, and wherein when the at least one tab is coupled to the receiving part, the spring element is configured to exert a compression force to urge the first and second engagement portions towards each other and towards the corresponding first and second engagement faces along a longitudinal axis defined by the combined tab and receiving part.

2. The extension device system according to claim 1, wherein the first engagement portion and the second engagement portion are shaped to provide a form-fit connection with the corresponding engagement faces of the receiving part.

3. The extension device system according to claim 1, wherein the coupling portion includes a tubular segment-shape to encompass an outer wall of a portion of at least one of the legs of the receiving part.

4. The extension device system according to claim 1, wherein the coupling portion of the at least one tab includes an aperture in which the spring element is arranged to be resiliently movable in the direction of the longitudinal axis, and wherein the spring element comprises at least a part of the first engagement portion or at least part of the second engagement portion.

5. The extension device system according to claim 1, wherein the coupling portion further includes a protrusion or a recess configured to mate with a corresponding recess or protrusion provided at an end portion of at least one of the legs of the receiving part, and wherein when the at least one tab is coupled to the receiving part, the recess or protrusion of the at least one of the legs is configured to prevent rotational movement of the receiving part with respect to the at least one tab.

6. The extension device system according to claim 1, wherein the spring element is arranged as a wave spring, a leaf spring, or a meandering spring.

7. The extension device system according to claim 1, wherein the elongate shaft portion has a tubular segment-shape having a first radius with respect to the longitudinal axis, the coupling portion has a tubular segment-shape having a second radius with respect to the longitudinal axis, and wherein the second radius is larger than the first radius.

8. The extension device system according to claim 1, wherein the second engagement portion is provided as an engagement face formed at a protrusion located at an inner wall adjacent the second end of the coupling portion.

9. The extension device system according to claim 8, wherein the engagement face of the second engagement portion is radially and/or outwardly inclined with respect to a plane perpendicular to the longitudinal axis.

10. The extension device system according to claim 1, wherein the first engagement portion is an engagement face of the spring element, and wherein the first engagement portion projects inwardly towards the longitudinal axis with respect to an inner wall adjacent the first end of the coupling portion.

11. The extension device system according to claim 1, wherein the first engagement portion is an engagement face of the spring element, and wherein the first engagement portion projects inwardly towards the longitudinal axis with respect to an inner wall adjacent the second end of the coupling portion.

12. The extension device system according to claim 1,
wherein the first engagement portion and the second engagement portion are both engagement faces formed at respective protrusions located at an inner wall of the coupling portion and are inclined or stepped with respect to a plane perpendicular to the longitudinal axis, wherein each of the engagement portions projects inwardly towards the longitudinal axis with respect to the inner wall adjacent the first end and the second end of the coupling portion, respectively, wherein each of the engagement portions is formed at a distinct section of the coupling portion, respectively, and wherein the spring element is connected between the sections.

13. The extension device system according to claim 1, wherein the at least one tab comprises two tabs, each tab configured to respectively couple to one of the two legs of the receiving part.

14. The extension device system according to claim 13, wherein the two tabs are separate parts.

15. The extension device system according to claim 13, wherein each leg of the receiving part includes a removable extension tab portion, and wherein the first engagement face and the second engagement face are respectively provided at the removable extension tab portions of the legs.

16. The extension device system according to claim 15, wherein the removable extension tab portions are configured to be removed by exerting a leverage force via the tabs onto the removable extension tab portions to break off the removable extension tab portions from other portions of the legs at predetermined breaking points.

17. The extension device system according to claim 1, wherein the at least one tab is monolithic.

18. An extension device system comprising:
a receiving part of a bone anchor, the receiving part comprising two legs defining a channel for receiving a rod, wherein each leg includes a first engagement face and a second engagement face; and two separable tabs, each tab comprising:
an elongate shaft portion that forms part of a channel for guiding surgical implants to the receiving part; and a coupling portion provided at a distal end of the elongate shaft portion, wherein the coupling portion includes a first engagement portion configured to engage the first engagement face of the receiving part, and a second engagement portion configured to engage the second engagement face of the receiving part, wherein the first engagement portion is axially between the second engagement portion and the elongate shaft portion;

wherein a spring element of a first one of the tabs is configured to exert a compression force to urge the first and second engagement portions of the first tab towards each other along a longitudinal axis defined by the first tab and the receiving part when coupled together.

19. An extension device for a bone anchor, the bone anchor including a receiving part for receiving a rod, the extension device comprising:

at least one monolithic tab comprising:
- an elongate shaft portion that forms part of a channel for guiding surgical implants to the bone anchor; and
- a coupling portion provided at a distal end of the elongate shaft portion, wherein the coupling portion includes a first end, a second end, a longitudinal axis extending between the first and second ends and through the elongate shaft portion, a first engagement portion configured to engage a first engagement face of the receiving part, and a second engagement portion configured to engage a second engagement face of the receiving part;

wherein a spring element of the at least one tab is axially aligned with at least an opposing part of the first engagement portion or at least an opposing part of the second engagement portion, and wherein the spring element is axially movable along the longitudinal axis relative to another portion of the at least one tab.

20. The extension device according to claim 19, wherein the spring element comprises at least a part of the first engagement portion or at least part of the second engagement portion.

21. A method of connecting an extension device to a bone anchor, the bone anchor comprising a receiving part having two legs defining a channel for receiving a rod, wherein each leg includes a first engagement face and a second engagement face, the extension device comprising at least one tab comprising an elongate shaft portion that forms part of a channel for guiding surgical implants to the receiving part, a coupling portion provided at a distal end of the elongate shaft portion, wherein the coupling portion includes a first end, a second end, a longitudinal axis extending between the first and second ends, a first engagement portion at the first end configured to engage the first engagement face of the receiving part, and a second engagement portion at the second end configured to engage the second engagement face of the receiving part, wherein the first engagement portion is axially between the second engagement portion and the elongate shaft portion, and wherein a spring element is provided at the coupling portion, the spring element configured to exert a compression force to urge the first and second engagement portions towards each other along the longitudinal axis, the method comprising:
- attaching one of the first or second engagement portions of the at least one tab to the first or second engagement faces of the receiving part;
- exerting a compression force by the spring element to urge the first and second engagement portions towards each other along the longitudinal axis; and
- attaching the other of the first or second engagement portions of the at least one tab to the other of the first or second engagement faces of the receiving part.

* * * * *

UNITED STATES PATENT AND TRADEMARK OFFICE
CERTIFICATE OF CORRECTION

PATENT NO. : 9,999,451 B2
APPLICATION NO. : 15/183641
DATED : June 19, 2018
INVENTOR(S) : Timo Biedermann et al.

Page 1 of 1

It is certified that error appears in the above-identified patent and that said Letters Patent is hereby corrected as shown below:

On the Title Page
Column 2, item (57), Abstract, Line 16    after "when" delete "being"

In the Specification
Column 6, Line 26    delete "1512," and insert -- 151a, --

Signed and Sealed this
Thirtieth Day of July, 2019

Andrei Iancu
*Director of the United States Patent and Trademark Office*